United States Patent
Miller et al.

(10) Patent No.: US 10,799,393 B2
(45) Date of Patent: Oct. 13, 2020

(54) LASER SURGERY APPARATUS FOR CONTACT LASER SURGERY

(71) Applicant: Max-Planck-Gesellschaft zur Foerderung der Wissenschaften e.V., Munich (DE)

(72) Inventors: R. J. Dwayne Miller, Hamburg (DE); Stephanie Maier, Hamburg (DE); Sebastian Kruber, Hamburg (DE); Nils-Owe Hansen, Hamburg (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 222 days.

(21) Appl. No.: 15/557,552

(22) PCT Filed: Feb. 19, 2016

(86) PCT No.: PCT/EP2016/000291
§ 371 (c)(1),
(2) Date: Sep. 12, 2017

(87) PCT Pub. No.: WO2016/146237
PCT Pub. Date: Sep. 22, 2016

(65) Prior Publication Data
US 2018/0055690 A1    Mar. 1, 2018

(30) Foreign Application Priority Data
Mar. 13, 2015    (EP) .................................. 15000757

(51) Int. Cl.
*A61B 18/20*    (2006.01)
*A61F 9/008*    (2006.01)
(Continued)

(52) U.S. Cl.
CPC ........ *A61F 9/00821* (2013.01); *A61B 18/203* (2013.01); *A61F 9/009* (2013.01);
(Continued)

(58) Field of Classification Search
CPC .................................................... A61C 1/0046
See application file for complete search history.

(56) References Cited

U.S. PATENT DOCUMENTS

| 4,126,136 A | 11/1978 | Auth et al. |
| 4,627,435 A | 12/1986 | Hoskin |

(Continued)

FOREIGN PATENT DOCUMENTS

| EP | 2226031 A1 | 9/2010 |
| WO | 0187176 A1 | 11/2001 |
| WO | 03009767 A1 | 2/2003 |

OTHER PUBLICATIONS

Amini-Nik et al. (2010). Ultrafast mid-IR laser scalpel: protein signals of the fundamental limits to minimally invasive surgery. PLoS One, 5(9), e13053: 1-6.
(Continued)

*Primary Examiner* — Lynsey C Eiseman
(74) *Attorney, Agent, or Firm* — Caesar Rivise, PC

(57) ABSTRACT

The present invention relates to a laser surgery apparatus for contact laser surgery and to a method of using the laser surgery apparatus. The laser surgery apparatus (1) comprises a contact laser scalpel (3) for contact laser surgery, the contact laser scalpel (4) comprising an optical fiber (4) of IR laser radiation transmissive material and terminating at an optical fiber tip (5) having an exposed core region, and support means for holding said fiber and for positioning said scalpel (3). Said fiber tip (5) is tapered and disposed at a distal end of the scalpel (3) for contacting a tissue to be cut and comprises an uncoated contact surface (6) for transmit
(Continued)

ting laser radiation and a guiding surface that is at least partially reflective to laser radiation and provided such that laser radiation guided by said optical fiber (4) to said fiber tip (5) will be at least partially reflected by said guiding surface and emitted through said uncoated contact surface. The contact laser surgery apparatus further comprises a pulsed laser source (2) adapted to provide pulse durations in the femtosecond, picosecond and/or nanosecond range, and light transmitting means (9) connecting said laser source (2) to said optical fiber (4) of said scalpel (3) for conveying laser radiation from said laser source (2) to said optical fiber (4) such that the conveyed laser light is emitted at said uncoated contact surface of the fiber tip.

24 Claims, 4 Drawing Sheets

(51) Int. Cl.
| | | |
|---|---|---|
| *A61N 5/06* | (2006.01) | |
| *A61F 9/009* | (2006.01) | |
| *A61B 18/22* | (2006.01) | |
| *A61B 18/00* | (2006.01) | |
| *A61N 5/067* | (2006.01) | |
| *A61B 17/3211* | (2006.01) | |

(52) U.S. Cl.
CPC ........ *A61F 9/00802* (2013.01); *A61N 5/0625* (2013.01); *A61B 17/3211* (2013.01); *A61B 2018/00107* (2013.01); *A61B 2018/225* (2013.01); *A61B 2018/2233* (2013.01); *A61B 2018/2272* (2013.01); *A61B 2018/2288* (2013.01); *A61F 9/00836* (2013.01); *A61F 2009/00861* (2013.01); *A61N 2005/063* (2013.01); *A61N 2005/067* (2013.01); *A61N 2005/0644* (2013.01)

(56) References Cited

U.S. PATENT DOCUMENTS

| | | | | |
|---|---|---|---|---|
| 4,672,969 | A * | 6/1987 | Dew | ................ A61B 17/00491 |
| | | | | 607/89 |
| 4,736,743 | A | 4/1988 | Daikuzono | |
| 5,951,543 | A * | 9/1999 | Brauer | ................ A61B 18/201 |
| | | | | 606/10 |
| 2006/0153254 | A1* | 7/2006 | Franjic | .................. B23K 26/38 |
| | | | | 372/30 |
| 2010/0286672 | A1 | 11/2010 | Walker et al. | |
| 2012/0135368 | A1* | 5/2012 | Rizoiu | .................. A61B 18/22 |
| | | | | 433/29 |

OTHER PUBLICATIONS

Clarkin et al. (2004). Shaped fiber tips for medical and industrial applications. In Proc. of SPIE Vol (vol. 5317, p. 70-80).

Decombe et al. (2013). Transmission and reflection characteristics of metal-coated optical fiber tip pairs. Applied optics, 52(26), 6620-6625.

Ding et al. (2007). Internal excitation and superfocusing of surface plasmon polaritons on a silver-coated optical fiber tip. Physical Review A, 75(6), 063822:1-10.

Franjic et al. (2009). Laser selective cutting of biological tissues by impulsive heat deposition through ultrafast vibrational excitations. Optics express, 17(25), 22937-22959.

Franjic et al. (2010). Vibrationally excited ultrafast thermodynamic phase transitions at the water/air interface. Physical Chemistry Chemical Physics, 12(20), 5225-5239.

Ilev et al. (2001). Evanescent-wave delivery into a precise tissue area using fiber optic probes. Proc. SPIE 4253, Optical Fibers and Sensors for Medical Applications, 161-167.

Janunts et al. (2005). Excitation and superfocusing of surface plasmon polaritons on a silver-coated optical fiber tip. Optics communications, 253(1), 118-124.

Lienau et al. (1996). Light-induced expansion of fiber tips in near-field scanning optical microscopy. Applied physics letters, 69(3), 325-327.

Sherman et al. (2000). Ultracision®: the harmonic scalpel and its possible uses in maxillofacial surgery. British Journal of Oral and Maxillofacial Surgery, 38(5), 530-532.

European Search Report from corresponding EP 15000757 dated May 12, 2015.

International Search Report from corresponding PCT/EP2016/000291 dated Apr. 22, 2016.

\* cited by examiner

LASER SURGERY APPARATUS FOR CONTACT LASER SURGERY

CROSS-REFERENCE TO RELATED APPLICATIONS

This application is a U.S. National Phase Application of PCT/EP2016/000291, filed Feb. 19, 2016, which claims priority to EP 15000757.3, filed Mar. 13, 2015, the contents of which applications are incorporated herein by reference in their entireties for all purposes.

FIELD OF THE INVENTION

The present invention relates to a laser surgery apparatus for contact laser surgery and to a method of using the laser surgery apparatus.

BACKGROUND OF THE INVENTION

In the present specification, reference is made to the following prior art illustrating the technical background.

[1] S. Amini-Nik, D. Kraemer, M. L. Cowan, K. Gunaratne, P. Nadesan, B. a Alman, and R. J. D. Miller, "Ultrafast mid-IR laser scalpel: Protein signals of the fundamental limits to minimally invasive surgery," PLoS One, vol. 5, no. 9, pp. 1-6, January 2010.

[2] K. Franjic, M. L. Cowan, D. Kraemer, and R. J. D. Miller, "Laser selective cutting of biological tissues by impulsive heat deposition through ultrafast vibrational excitations," Opt. Express, vol. 17, no. 25, pp. 22937-59, December 2009.

[3] J. a Sherman and H. T. Davies, "Ultracision: The harmonic scalpel and its possible uses in maxillofacial surgery," Br. J. Oral Maxillofac. Surg., vol. 38, no. 5, pp. 530-2, October 2000.

[4] F. Robert, "U.S. Pat. No. 4,126,136 A—Photocoagulating scalpel system," 1978.

[5] P. E. F. Hindenburg, "U.S. Pat. No. 4,736,743 Vaporization contact laser probe," 1988.

[6] FRANJIC, Kresimir; MILLER, R J Dwayne. "Vibrationally excited ultrafast thermodynamic phase transitions at the water/air interface". Physical Chemistry Chemical Physics, 2010, 12. Jg., Nr. 20, S. 5225-5239.

Mechanical scalpels are used to create fine incisions primarily in skin tissues. In strongly perfused tissue electrocautery and laser surgery systems are dominant compared with a mechanical scalpel due to simultaneous coagulation.

Conventional fiber optic laser surgery systems generally fall within one of two broad classes, contact systems and free beam systems. Contact systems, as the name suggests, utilize a contact element (i.e. an optical fiber tip or a lens element), which is placed in contact with a tissue area to be irradiated, and a beam carried by the fiber is delivered to the tissue at the point of contact. One exemplary type of contact system is the "ball tipped" system, which generally comprises an optical fiber tip having an exposed core region, which is formed into the shape of a ball. In use, the ball of the fiber tip is placed in contact with the tissue to be irradiated, and substantially all of the energy delivered to the tip of the fiber is delivered to the tissue at the point of contact. It will be noted by those skilled in the art that, as the radiation passes directly from the laser fiber to the tissue to be treated, only a minimal amount of energy is lost at the tissue-fiber interface. However, as substantially all of the laser energy is delivered to the tissue at the point of contact (i.e. as substantially all of the laser energy is delivered to an extremely small tissue area), the use of contact delivery systems often results in excessive tissue vaporization and carbonization, thus making it quite difficult to treat large tissue areas in an even fashion.

For example, the prior art reference [5] discloses a medical laser probe for contact laser surgery wherein the medical laser probe has a probe tip coated with infrared adsorbing material and cuts by direct and indirect laser heating of the tissue. Direct laser irradiation causes the direct heating and the absorbed laser energy in the coating heats the tip itself and causes the indirect heating of the tissue. Both heating mechanisms vaporize the tissue. This mechanism cuts by slow heating with significant damage to surrounding tissue.

A newer approach is the ultracision scalpel, a scalpel in shape of a scissor with ultrasonic technology, which is described in reference [3]. The photocoagulating scalpel system described in reference [4] discloses a scalpel having a sharp transparent blade with an optically coupled laser for coagulating the surrounding tissue of the incision.

The different cutting modalities are based on different mechanisms. A mechanical scalpel cuts skin by inducing shear stress over the elastic limit of the tissue. In electrocautery the tissue is melted by a tiny wire loop heated by an electric current. Most of the medical lasers also melt tissue by depositing heat and cause damage zones up to 800 micrometer according to reference [1]. According to reference [2], the new generations of pulsed medical lasers ablate tissue with a smaller damage zone in the adjacent tissue in the range of micrometers, but suffer from ionization of the tissue creating toxic free radicals or missing coagulation to stop bleeding. According to reference [3], the above-mentioned ultracision scalpel cuts and simultaneously coagulates by locally deposited heat in the range of 70 to 100° C. These different mechanisms either cause excessive damage to surrounding tissue (cold instruments such as scalpels via shearing tissue, hot instruments or long pulsed (>1 ns) lasers via burning, femtosecond lasers by ionization) or involve complex scanning systems (all laser systems).

OBJECTIVE OF THE INVENTION

The contact laser scalpel of the present invention has been developed to overcome the above-mentioned known problems associated with conventional mechanical and laser scalpels. Accordingly, it is an object of the invention to provide an improved scalpel which is capable of performing tissue incision minimal damage to surrounding tissue and which represents an intuitive tool for surgery that has the ease of use of cold steel tools.

SUMMARY OF THE INVENTION

The above objectives are solved by a laser surgery apparatus for contact laser surgery and a method of using the laser surgery apparatus of the invention.

According to a first general aspect of the invention, the above objective is solved by a laser surgery apparatus for contact laser surgery. The contact laser scalpel comprises an optical fiber of IR laser radiation transmissive material that terminates at an optical fiber tip having an exposed core region, i.e. the fiber tip is not surrounded by a cladding material. The contact laser scalpel further comprises support means for holding said fiber and for positioning said scalpel.

The fiber tip is tapered and disposed at a distal end of the scalpel for contacting a tissue to be cut and comprises an uncoated contact surface for transmitting laser radiation and a guiding surface that is at least partially reflective to laser radiation and provided such that laser radiation guided by said optical fiber to said fiber tip will be at least partially reflected by said guiding surface and emitted through said uncoated contact surface. The fiber tip is made of the material of the fiber core, resulting in no interface between the shape and the fiber itself.

The contact laser scalpel further comprises a pulsed laser source adapted to provide pulse durations in the femtosecond, picosecond and/or nanosecond range, and light transmitting means connecting said laser source to said optical fiber of said scalpel for conveying laser radiation from said laser source to said optical fiber such that the conveyed laser light is emitted at said uncoated contact surface of the fiber tip.

Preferably, the wavelength, pulse duration and repetition rate of the laser source are set such that when said uncoated contact surface of the fiber tip contacts a tissue to be cut, a fluence of the pulsed laser radiation is under the ablation threshold of a given tissue. By way of example only, the fluence is under the ablation threshold of a biological or human tissue.

By contrast, for conventional contact laser systems, irradiation of the tissue at dose levels of 1 J/cm^2 is needed. This corresponds to heating the tissue several times above the critical phase transition temperature. According to reference [6], for conventional and known infrared laser systems with a picosecond infrared laser (PIRL) source as the most efficient example, laser fluences corresponding to superheating of at least four times the boiling phase transition are needed. This excess energy above lattice disruption leads to the need for expensive higher power lasers as well as complex expensive beam delivery systems and some associated excessive tissue damage due to imperfect beam deliver conditions within the occluded view of an operation.

It is therefore a particular advantage of the present invention that such excessive tissue damage can be avoided by proposing that the fluence of the pulsed laser radiation be under an ablation threshold of a given tissue, which is four times less than typical.

According to a preferred aspect of the invention, the wavelength, pulse duration and repetition rate of the laser source are set such that when said uncoated contact surface of the fiber tip contacts a tissue to be cut, pulsed IR laser radiation of the pulsed laser source emitted from the uncoated contact surface of the fiber tip heats water in the contacted tissue to a temperature in the range of 50° C. to <200° C. and/or heats biological tissue up to a temperature below a vaporization temperature of the tissue in the range from 100° C. for soft tissue to 1500° C. for bony and calcified structures or teeth and thereby reduces the shear force needed for cutting the tissue.

In other words, according to this aspect, the invention proposes to superheat the tissue to be cut using pulsed IR laser radiation so that at the ultrafast temperature jump point, the lattice of the tissue in contact with the fiber tip is no longer bound. It is superheated and any perturbation will lead to lattice disruption and cutting. The elasticity of the tissue at this point collapses to near zero so that the force normally needed to cut tissue locally in this region also collapses to near zero or is at least dramatically reduced.

Thus, according to an aspect of the invention, the wavelength, pulse duration and repetition rate of the laser source are set such that when said uncoated contact surface of the fiber tip contacts a tissue to be cut, a surgical incision can be made by (a) providing local impulsive heating of the water in the contacted tissue by pulsed IR laser radiation of the laser source and (b) by simultaneously or subsequently applying a shear force using the uncoated contact surface of the fiber tip as a mechanical cutting edge to locally cut the heated tissue.

The key feature at this point is that the tissue no longer needs to experience sufficient shear force to tear, which is the actual mechanism of cutting with a scalpel. It will locally experience sufficient shear or transverse force from the fiber tip serving also as a mechanical cutting edge to locally separate or be effectively cut.

Due to the reduced fluence under the ablation threshold, the tissue is locally heated in a range under the ablation threshold to weaken the hydrogen bonds in the water within the tissue and colligative forces of the connective tissue to reduce the mesh tension to cut with the blade-like fiber tip shape. This reduced temperature is well below the combustion point of the tissue in fully oxygenated air, however, it is high enough to lead to local coagulation of the tissue. In contrast to laser ablation, these locally heated proteins and constituent biopolymer matrix are not removed during the cutting process, but remain as a heated biopolymer to help stop bleeding through coagulation.

This is a major distinction over conventional cold instruments in which the tissue is displaced and stretched past the elasticity point at which point it tears or is cut. This stretching with accompanying heating typically extends out beyond 400 microns, which in turn causes cell damage and the formation of scar tissue. By contrast, the contact laser scalpel of the present invention, when in use, locally reduces all the required shearing motion to cut the region of the hybrid laser scalpel contact region, which is less than 10 microns or the dimensions of a single cell.

This invention therefore introduces a new hybrid concept in which the addition of mechanical forces simultaneous with or immediately after the ultrafast laser heating of the water in the tissue collapses the shear forces needed to cut the tissue to near zero and enables cutting at the level of a single cell without damage to surrounding tissue—preferably all in a hand held device.

According to a preferred embodiment of the invention, the pulsed laser source is a picosecond infrared laser (PIRL) source. A PIRL source provides ultrafast laser heating to cut at the lowest possible laser fluence. According to this embodiment, the PIRL source may be configured to generate pulsed IR laser light of a wavelength falling within a range from 1 µm to 20 µm, of a pulse duration falling within a range from 100 fs to 10 ns, and of a repetition rate falling within a range from 1 Hz to 1 MHz.

It will be understood by those skilled in the art that the wavelength, pulse duration and repetition rate will be set to appropriate values falling within these ranges depending on the biological tissue to be cut. As mentioned above, in order to heat the tissue to be cut to a temperature below a vaporization temperature of the tissue, temperatures in the range from 100° C. for soft tissue to 1500° C. for bony and calcified structures and teeth might be required.

By way example only, the PIRL laser source may be configured to provide pulsed IR laser light of a wavelength in the range of 1 µm-20 µm, but especially 3 µm for heating $H_2O$ and 6 µm for heating connective tissue to be cut.

According to a further aspect of the invention, the contact laser scalpel is a hand-held portable scalpel and/or the support means is formed as a handpiece with which the contact laser scalpel can be moved or used by hand. This has the advantage that a contact laser scalpel is provided that has the intuitive ease of use of cold steel tools.

In another variant, the contact laser scalpel may be a portable scalpel, configured to be guided by a surgical robot.

In yet another variant, the contact laser scalpel may be a non-portable scalpel, configured to be guided by a surgical robot. In this case, the support means may be formed as a guiding and holding device for automatically positioning and guiding the laser scalpel by the surgical robot control unit.

According to a further aspect of the invention, the uncoated surface may have a diameter of less than 100 μm, preferably a diameter of less than 10 μm in order to enable cutting at the dimensions of a single cell.

According to another aspect of the invention, the fiber tip may have a blade shape of a mechanical scalpel and the uncoated contact surface of the fiber tip is arranged at the location of the cutting section or cutting edge of the blade shape. An advantage of this aspect is that the design of the fiber tip is not only optimized for beam delivery, but since it is also used for mechanical cutting, it also takes into account the most important features of conventional blades, scissors, needles and other instruments used in surgery. By way of example, the fiber tip may have a wedge shape, a hook shape, a conical shape, a chisel shape, a shape of a side cutting blade, or a needle shape.

According to yet another aspect of the invention, said guiding surface of the fiber tip is a coated surface that is reflective to laser radiation and provided such that laser radiation guided by said optical fiber to said fiber tip will be reflected by said coated surface and emitted through said uncoated surface. The reflective coating forms a reflective cavity for the laser energy inside the tapered and exposed fiber core of the fiber tip through which incoming laser radiation is channelled through multiple reflections within this cavity to the uncoated surface. With the coating, unwanted radiation losses of laser radiation due to the taper of the exposed fiber tip can be avoided, i.e. losing light that exceeds the critical angle for total internal reflection in the tapered optical fiber tip and would thus not be emitted through the uncoated contact surface but through the guiding surface. Through coating of selected surfaces, it could be defined at which surface the light is emitted from the fiber tip, i.e. the uncoated contact surface. Therefore the laser light can be precisely applied and too high energy losses can be avoided.

By way of example, the coated surface may have a metallic coating, a stacked oxide coating, and/or a dielectric coating for the infrared region. An additional protective coating may be provided on top of the reflective coating.

In a preferred variant of this aspect of the invention, the fiber tip is wedge-shaped having a planar rectangular uncoated end surface at the distal end of the scalpel forming the uncoated contact surface and a coated slant surface formed at an angle with respect to the end surface and converging in a direction of the end surface.

In an alternative variant of this aspect, the fiber tip has a chisel shape. According to this alternative variant, the contact laser scalpel further comprises a second optical fiber terminating at a second optical fiber tip. The second optical fiber tip is arranged in parallel and adjacent to the first fiber tip. The two fiber tips are conical-shaped, the conical surface of each fiber tip being coated except for a line segment joining the apex to the perimeter of the large diameter end portion of the conical surface, and the uncoated line segments of the two fiber tips being arranged facing each other and forming a V-shaped uncoated contact area, thus serving as the mechanical cutting edges of the fiber tip.

The guiding surface of the fiber tip does not necessarily have to be a coated surface. According to an alternative embodiment, said guiding surface is an uncoated surface having a tapering angle such that at least 30% of laser radiation guided by said optical fiber to said fiber tip will be reflected by said guiding surface and subsequently emitted through said uncoated contact surface.

According to this embodiment, the tapering of the optical fiber tip is restricted to tapering angles that limit the portion of incoming laser radiation that exceeds the critical angle for total internal reflection in the tapered optical fiber tip and is thus not emitted through the uncoated contact surface but through the guiding surface to below 70% of the incoming laser radiation. By way of example, in case the optical fiber is a sapphire (Al2O3) fiber, a tapering angle that is lower than 15°, preferably lower than 11°, can be used. If the width of the fiber tip core at the entry edge is W1, the width at the exit edge is W0, and the length of the taper of the fiber tip core is L, then the tapering angle α is defined by the following equation: $\tan \alpha = (W1 - W0)/2L$.

According to further aspects of the invention, the optical fiber tip may be made of a IR laser radiation transmissive material, such as $Al_2O_3$ (Sapphire), $Y_3Al_5O_{15}$ (YAG), $GeO_2$ (Germanium Oxid), $TeO_2$ (Telluriumoxid), $ZrF_4$, $InF_3$, $AlF_3$, endcapped PCF or endcapped hollow core fibers, or other infrared waveguiding fibers. Preferably, the fiber tip is made of a material that is intrinsically very hard or at least hard.

The diameter of a guiding fiber core of the optical fiber may be in the range of 4 to 1000 μm prior to any tapering or structuring of the fibre tip. The optical fiber may also be a single mode fiber. In this case, a diameter of a fiber core is in the range of 1 to 100 μm.

According to yet another aspect of the invention, the laser surgery apparatus may comprise an input terminal for selecting a type of tissue to be cut and a laser source control unit being configured for controlling a wavelength, pulse duration and/or a repetition rate of the generated laser radiation based on the selected type of tissue. This has the advantage that the laser fluence under the ablation threshold can be automatically adjusted to preselected levels based on the tissue to be cut in order to ensure that the tissue is locally heated to reduce the shear force to cut the tissue to zero or almost zero locally under the applied tip.

According to a second general aspect of the invention, the above objective is solved by a method of using the laser surgery apparatus according to any of the aspects disclosed herein. The method comprises the steps of contacting a tissue to be cut with the uncoated surface of the fiber tip of the scalpel and making an incision by heating the contacted tissue by pulsed IR laser radiation of the laser source emitted from the uncoated surface, wherein the water in contacted tissue is heated to a temperature in the range of 50° C. to <200° C. and/or to a temperature below a vaporization or boiling point temperature of the contacted tissue in the range from 100 to 1500° C. for tissue varying from soft tissue to bony and calcified structures/teeth and thereby reducing the shear force needed for cutting the tissue.

In other words, the tissue to be cut is superheated by using pulsed IR laser radiation so that at the ultrafast temperature jump point, the lattice of the tissue in contact with the fiber tip is no longer bound. Any perturbation to the superheated tissue will lead to lattice disruption and cutting. The elasticity of the tissue at this point collapses to near zero so that the force normally needed to cut tissue locally in this region also collapses to near zero or is at least dramatically reduced.

Simultaneously or subsequently to the heating, the method further comprises the step of cutting the heated tissue in the region below the uncoated surface of the fiber tip by locally exerting a mechanical shearing force with the fiber tip.

BRIEF DESCRIPTION OF THE DRAWINGS

Further details and advantages of the invention will be described in the following with reference to the attached drawings, which show in.

DESCRIPTION OF THE PREFERRED EMBODIMENTS

Figure 1:
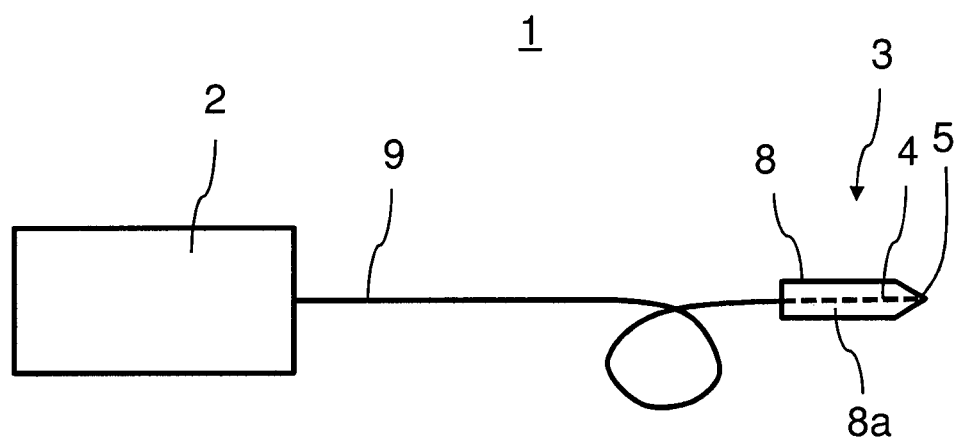
FIG. 1: a schematic illustration of an embodiment of a laser surgery apparatus for contact laser surgery according to the invention.

FIG. 1 shows a schematic illustration of an embodiment of a laser surgery apparatus 1 for contact laser surgery according to the invention.

The laser surgery apparatus 1 comprises a picosecond infrared laser (PIRL) source 2 that is configured to generate pulsed IR laser light of a wavelength falling within a range from 1 µm to 20 µm, of a pulse duration falling within a range from 100 fs to 10 ns, and of a repetition rate falling within a range from 1 Hz to 1 MHz.

The laser surgery apparatus 1 further comprises a contact laser scalpel 3 for contact laser surgery that comprises an optical fiber 4 of IR laser radiation transmissive material which terminates at an optical fiber tip 5. The fiber tip 5 comprises an exposed core region that is tapered and has a form of a mechanical blade shape (cf. FIGS. 2A to 3F) and is disposed at a distal end of the scalpel 3 for contacting a tissue to be cut. Thus, the shaped fiber tip 5 extends forwardly of the handpiece 8 to define a surgical cutting surface.

The contact laser scalpel 3 is a hand-held portable scalpel and comprises a handpiece or hand support 8, which the surgeon holds during surgery and with which the contact laser scalpel can be moved or used by hand. The shape of the hand support can be of conventional design. The optical fiber 4 is fastened to the handpiece 8 by providing a hole or passage 8a through the handpiece 8 along the longitudinal scalpel axis through which an extended portion of fiber 4 is passed (which is schematically illustrated in FIG. 1 by the dashed line). This hole is of appropriate diameter to snugly receive fiber 4 therein. At the opposing end of the fiber tip 5, the fiber 4 is coupled to light transmitting means 9, e.g. another optical fiber, connecting the PIRL source 2 to the optical fiber 4 of the scalpel 3 for conveying laser radiation from said laser source 2 to the fiber tip 5.

The optical fiber 4 can be a multi-mode or a single-mode fiber comprising a core of relatively high refractive index, which is surrounded by a cladding of relatively low refractive index. At the portion of the fiber tip 5, the cladding is removed and/or not present. The fiber core is made of an IR laser radiation transmissive material, such as $Al_2O_3$, $Y_3Al_5O_{15}$, $GeO_2$, $TeO_2$, $ZrF_4$, $InF_3$, $AlF_3$, endcapped PCF or endcapped hollow core fibers, or other infrared waveguiding fibers.

It will be appreciated that the present extended fiber scalpel provides for the transmission of the laser energy from the laser source 2 to the point of operative tissue contact at the scalpel tip end, i.e. the contact surface 6 of fiber tip 5, along a single continuous fiber path without the fiber-to-scalpel interface often used in other contact laser instruments.

Figure 2A:
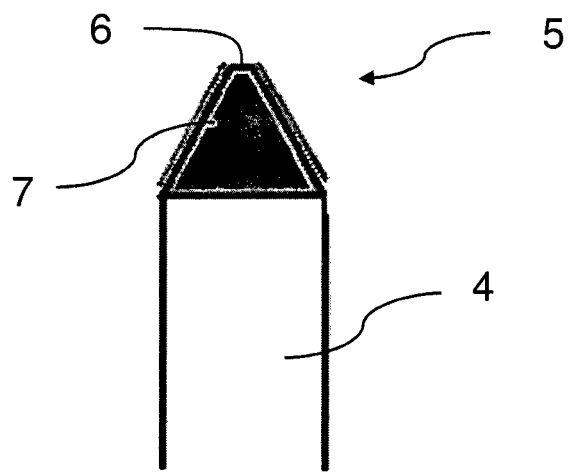
FIGS. 2A to 2C: schematic illustrations of a frontal view, a side view and a perspective view of a wedge-shaped fiber tip according to an embodiment of the invention.
Figure 2B:
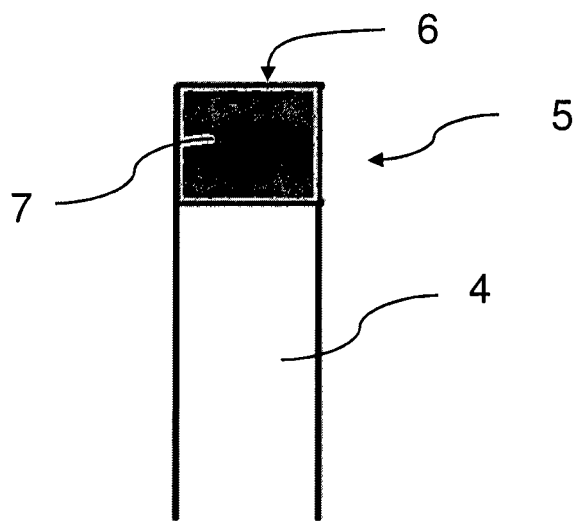

FIG. 2A shows an enlarged frontal view of the fiber tip 5 to schematically illustrate the elements of the fiber tip 5. FIG. 2B shows a corresponding side view and FIG. 2C a corresponding perspective view of the fiber tip 5.

The fiber tip 5 is tapered and disposed at a distal end of the scalpel 3 for contacting a tissue to be cut. The tip comprises an uncoated contact surface 6 for transmitting and emitting laser radiation and a coated surface 7 that is at least partially reflective to laser radiation and provided such that laser radiation guided by said optical fiber 4 to said fiber tip 5 will be reflected by said guiding surface and emitted through said uncoated contact surface 6. In the present embodiment, a metallic coating is used. Alternatively, a stacked oxide coating or a dielectric coating for the infrared region may be used.

The uncoated surface 6 has a diameter of less than 100 µm, preferably a diameter of less than 10 µm.

The fiber tip 5 shown in these figures has a wedge shape. However, it is emphasized that a wedge-shaped fiber tip is just one example of carrying out the invention, and the invention is not limited to this geometry.

When operating with laser surgery contact probes, surgeons use a variety of tip shapes, e.g. depending on the type of incision required, or special shapes for tissue removal and undercut. It will therefore be understood that other tip configurations corresponding to the conventional blade shapes of a mechanical scalpel, such as conical, chisel-shaped etc., may be used alternatively and are illustrated in FIGS. 3A to 3F. The uncoated contact surface 6 of the fiber tip is arranged at the location of the cutting section or cutting edge of the corresponding blade shape of the mechanical scalpel.

Figure 2C:
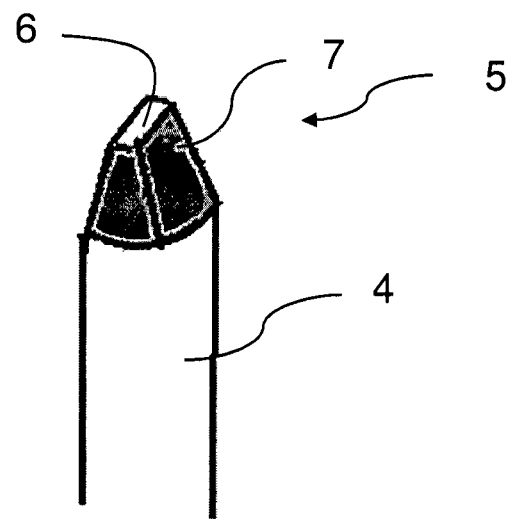
Figure 3:
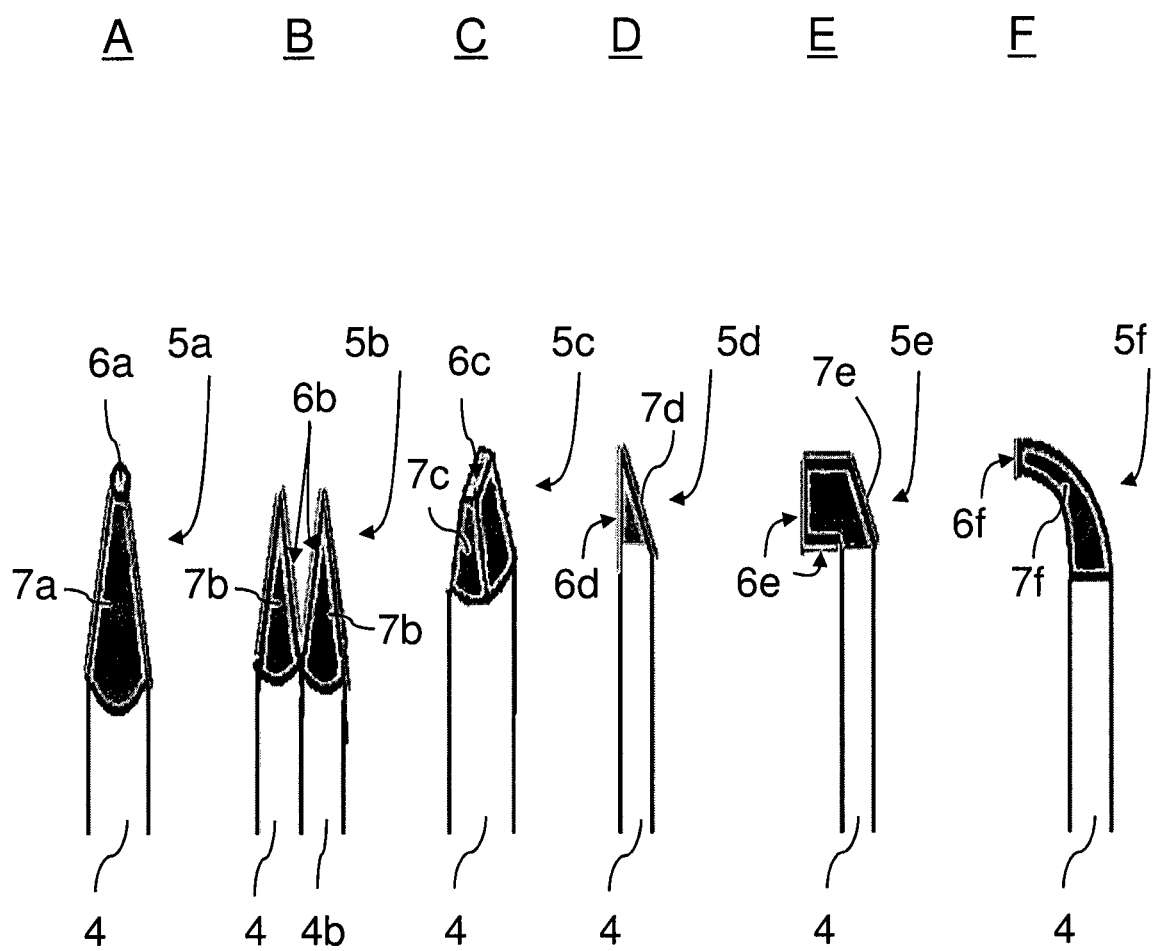
FIGS. 3A to 3F: schematic illustrations of further possible shapes of the optical fiber tip.

The fiber tip shown in FIGS. 2A to 2C corresponds to the fiber tip 5c shown in FIG. 3C. The fiber tip 5c has a planar rectangular uncoated end surface 6c at the distal end of the scalpel 3 forming the uncoated contact surface and coated slant surfaces 7c formed at an angle with respect to the end surface 6c and converging in a direction of the end surface 6c. The shaped fiber tip 5c enables to deposit the laser energy at the uncoated end of the fiber tip with a width of tens of micrometers at the interface to the tissue. The coating of the fiber tip 5c reflects the light guided in the fiber core 4 to the rectangular area 6c of the fiber tip.

The fiber tip 5a of FIG. 3A is conically tapered with a truncated tip, wherein the uncoated circular contact surface 6a is located at the truncated tip and the surface of the cone is coated with a reflective coating.

The fiber tip 5b shown in FIG. 3B has a chisel shape. The fiber tip 5b comprises a second optical fiber 4b terminating at a second optical fiber tip 5b. The second optical fiber tip 5b is arranged in parallel and adjacent to the first fiber tip. The two fiber tips 5b are conical-shaped, the conical surface of each fiber tip being coated except for a line segment 6b joining the apex to the perimeter of the large diameter end portion of the conical surface. The uncoated line segments 6b of the two fiber tips are arranged facing each other and form a V-shaped uncoated contact area serving as emitting surface for the pulsed laser radiation and also as mechanical cutting edge.

The fiber tips 5d and 5e shown in FIGS. 3D and 3E have the known shapes of a conventional mechanical side cutting blade. The side surface that corresponds to the location of the cutting side surface of the conventional mechanical side cutting blade are the uncoated contact surfaces 6d and 6e resp., the remaining surfaces 7d, 7e are coated with a reflective coating.

The fiber tip 5f shown in FIG. 3f has a hook shape wherein the uncoated contact surface 6f of the tip is located at a distal end the tip. The remaining surface 7f of the tip is coated with a reflective coating.

Various fabrication techniques are contemplated for the shaped fiber tips 5, 5a to 5f as shown in FIGS. 2A to 2C and 3A to 3F such as laser shaping of the end face of the fiber 4. The shaped fiber tips are machined or sculpted on the fiber end using the material of the fiber itself. Optionally, the end face can be polished. No additional glass material is added in the process. The process can be either mechanical or thermal in nature, the latter being primarily but not limited to laser machining/laser lensing.

Having no interface between the fiber tip and the rest of the fiber, there is no potential for contamination that might exist if the shape were bonded by fusion splicing to the fiber. This serves to reduce optical losses and dramatically increase the mechanical strength and durability of the device. However, it is also possible to form the tip by stretching an optical fiber while it is heated and providing a separate produced end cap spliced to the fiber end.

It is noted that shaped fiber tips for use in medical and industrial applications have already been known in the art for many years. Many different shaped tips have been successfully fabricated, as for example disclosed in "Shaped Fiber Tips for Medical and Industrial Applications", Clarkin et al., Optical Fibers and Sensors for Medical Applications IV, edited by Israel Gannot, Proceedings of SPIE Vol. 5317 (SPIE, Bellingham, Wash., 2004).

Companies offering laser lensing of optical fibers to create optical fibers with shaped fiber tips include OpTek Systems Inc., 12 Pilgrim Road, Greenville S.C., 29607, USA and WT&T Inc., 5550 Boulevard Thimens, Saint Laurent, Quebec, H4R 2K9, Canada.

Figure 4:
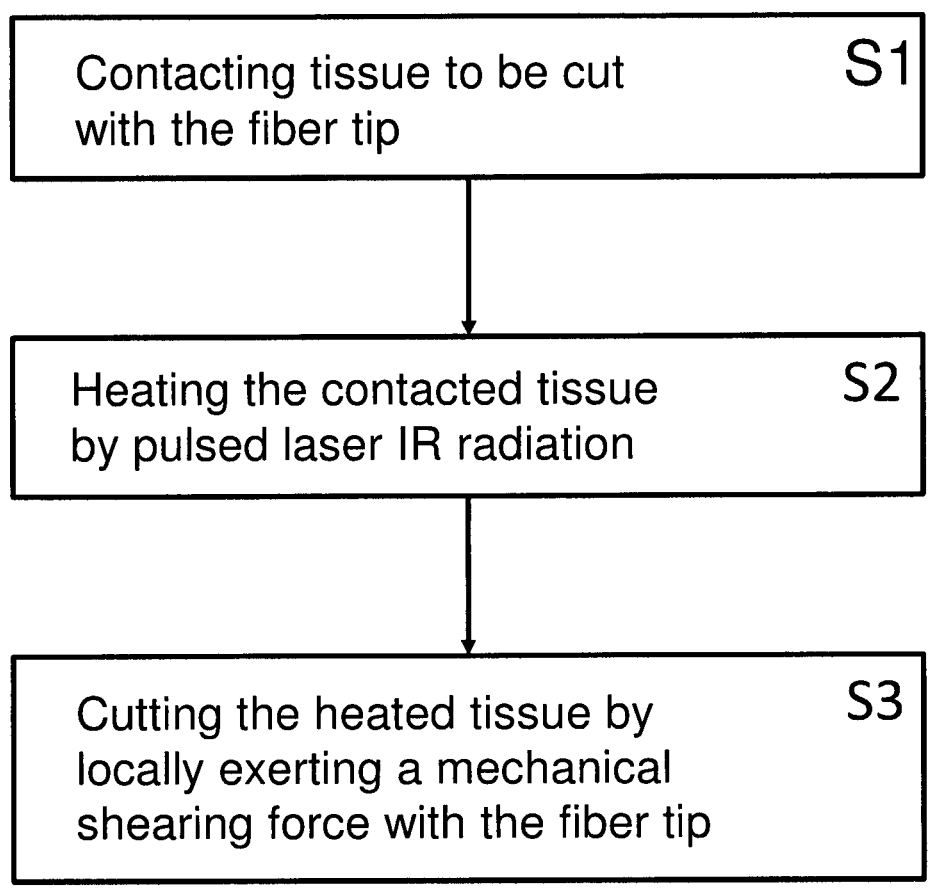
FIG. 4: a flow diagram of steps according to a method using the laser surgery apparatus.

FIG. 4 shows a flow diagram of steps according to a method using the laser surgery apparatus 1 as described above.

In use, the uncoated portion 6 of the contact tip 5 is applied directly to the tissue to be cut. The shaped optical fiber 5 serves both as a means to heat the tissue to be cut and as a mechanical cutting edge to make an incision.

In step S1, the handpiece 8 is thus used to position the fiber tip 5 on a tissue to be cut so that the uncoated contact surface 6 contacts the tissue.

In step S2, the contacted tissue is superheated by pulsed IR laser radiation of the laser source PIRL source 2 emitted from the uncoated surface 6 into the tissue, wherein the water in the contacted tissue is heated to a temperature in the range of 50° C. to <200° C. and/or to a temperature below a vaporization or boiling point temperature of the contacted tissue in the range from 100 to 1500° C. for tissue varying from soft tissue to bony and calcified structures/teeth and thereby reducing the shear force needed for cutting the tissue.

An incision can then be made in step S3 by simultaneously or subsequently cutting the heated tissue in the region below the uncoated surface 6 of the fiber tip by locally exerting a mechanical shearing force with the fiber tip 5.

In step S2, the virtues of a PIRL source are used to just heat the water in tissues to the boiling point (4× less than typical). This alone is a dramatic improvement in efficiency and reduces laser requirements to near laser pointer output power levels. At the ultrafast temperature jump point, the lattice is no longer bound. It is superheated and any perturbation will lead to lattice disruption and cutting. The elasticity of the tissue at this point collapses to near zero so that the force normally needed to cut tissue locally in this region also collapses to near zero or to an at least dramatically reduced force. The key feature at this point is that the tissue no longer needs to experience sufficient shear force to tear, the actual mechanism of cutting with a scalpel. It will locally experience sufficient shear or transverse force from this hybrid laser scalpel to locally separate or be effectively cut. This is a major distinction over conventional cold instruments in which the tissue is displaced and stretched past the elasticity point at which point it tears or is cut. This stretching with accompanying heating typically extends out beyond 400 microns, which in turn causes cell damage and the formation of scar tissue.

The present invention locally reduces all the required shearing motion to cut to the region of the hybrid laser scalpel contact region which is less than 10 microns or the dimensions of a single cell. Equally important, due to the reduced fluence under the ablation threshold, is that the tissue is locally heated in a range of 50 to 100° C. to weaken the hydrogen bonds in the water within the tissue and colligative forces of the connective tissue to reduce the mesh tension to cut with the blade-like fiber tip shape. This reduced temperature is well below the combustion point of the tissue in fully oxygenated air, however, it is high enough to lead to local coagulation of the tissue. In contrast to laser ablation, these locally heated proteins and constituent biopolymer matrix are not removed during the cutting process, but remain as a heated biopolymer to help stop bleeding through coagulation.

The present invention also avoids the disadvantages of laser surgery systems using a continuous wave (CW) laser source which heat the tissue on very long timescales that do not change the tissue's mechanical properties, and there is excessive heat transfer to the surrounding tissue that leads to cell damage and associated scar tissue. The same effect can be realized using electric current to heat the blade through resistive heating. There is no localization of the heat by virtue of ultrafast tissue disruption. The present invention explicitly uses the impulsive heating of water with an ultra-short IR pulse to reduce the shear force to cut the tissue to zero or almost zero locally under the applied tip. The tissue disruption in this region localizes the heat. The best analogy is to consider cutting asphalt with a jack hammer as opposed to trying to melt the asphalt. If asphalt were heated locally as fast as the jack hammer motion (in this case provided by the near explosive thermal expansion), there would be no crumbling of the asphalt and the cut would be defined by the dimension of the jack hammer bit—in the present case the fiber edge.

The surgical laser scalpel with a tapered and metallic coated fiber tip has the advantages of pulsed medical lasers, e.g. smaller damage zone, in comparison to electrocautery and conventional lasers. In addition, it avoids the typical disadvantages of pulsed lasers: Due to the reduced fluence, local coagulation of the tissue is achieved and ionization of tissue is avoided. This invention reduces the required laser fluence substantially, by up to an order of magnitude in comparison to some laser sources currently in use. This feature alone leads to much less tissue damage. It also provides the surgeon with a very intuitive tool for surgery that has all the ease of use of a cold steel tool but with orders of magnitude less tissue damage in order to enable scar free operations.

A further important advantage of the invention is that laser surgery cuts by ablation and the depth of cutting is limited by scattering as the cut gets deeper. Typically, the laser must be used in a trepanning mode in which the top tissue region must be widened as the cut is made deeper. This process leads to much slower cutting, much more loss of tissue than needed, and is difficult to control as tissue cutting varies with composition. By contrast, using the laser surgery apparatus of the present invention provides a self-guided shear force that opens up the tissue to allow deeper cutting without scattering losses, and avoids the use of other means of stretching the tissue to permit deeper cutting, as typically done with cold instruments.

Another advantage of the invention results from the fact that the laser surgery apparatus of the present invention can be used to cut at the phase transition threshold for water. As a consequence, there is no ablation debris to coat the optic. The device is in contact with tissue and tissue fluids and as such is self-cleaning without any need for means to protect the optics from ablation debris as required by other laser approaches that normally involve long working distances with aspiration to pick up the laser ablation plume. This represents an important advance of this device—in that it provides all the benefits of the state of the art PIRL scalpel for scar free cutting of tissue but with greatly reduced laser power and associated costs.

Thus, a new hybrid concept is proposed in which a hand-held device 3 is used to both give the surgeon complete freedom and laser coupling of a PIRL source to cut at the lowest possible laser fluence. The addition of mechanical forces simultaneously with the ultrafast laser heating of the water in the tissue collapses the shear forces needed to cut the tissue to near zero and enables cutting at the level of single cell without damage to surrounding tissue.

The invention claimed is:

1. A laser surgery apparatus for contact laser surgery, comprising
   a) a contact laser scalpel for contact laser surgery, the contact laser scalpel comprising:
      an optical fiber of IR laser radiation transmissive material and terminating at an optical fiber tip having an exposed core region, and
      a support for holding said optical fiber and for positioning said contact laser scalpel, wherein
      said optical fiber tip being tapered and disposed at a distal end of the contact laser scalpel for contacting a tissue to be cut and comprising an uncoated contact surface for transmitting laser radiation and a guiding surface that is at least partially reflective to laser radiation and provided such that laser radiation guided by said optical fiber to said optical fiber tip will be at least partially reflected by said guiding surface and emitted through said uncoated contact surface;
   b) a pulsed laser source configured to provide pulse durations in the femtosecond, picosecond and/or nanosecond range, and
   c) a light transmitting device connecting said laser source to said optical fiber of said contact laser scalpel for conveying laser radiation from said laser source to said optical fiber such that the conveyed laser light is emitted at said uncoated contact surface of the optical fiber tip,
      wherein the uncoated contact surface of the optical fiber tip is arranged at a location of a cutting section, and wherein said guiding surface is located around an entire periphery of the optical fiber tip and provided such that laser radiation guided by said optical fiber to said optical fiber tip will be reflected by said guiding surface and emitted through said uncoated contact surface such that a majority of laser energy is emitted along a fiber optical axis through the uncoated contact surface.

2. The laser surgery apparatus according to claim 1, wherein said pulsed laser source is a picosecond infrared laser (PIRL) source.

3. The laser surgery apparatus according to claim 2, the PIRL source being configured to generate pulsed IR laser light
   a) of a wavelength falling within a range from 1 μm to 20 μm,
   b) of a pulse duration falling within a range from 100 fs to 10 ns, and
   c) of a repetition rate falling within a range from 1 Hz to 1 MHz.

4. The laser surgery apparatus of claim 2, wherein the PIRL laser source is configured to provide pulsed IR laser light of at least one of 3 μm and 6 μm wavelength.

5. The laser surgery apparatus according to claim 1, wherein the contact laser scalpel is at least one of a portable scalpel, configured to be guided by a surgical robot and a hand-held portable scalpel.

6. The laser surgery apparatus according to claim 1, wherein the support is formed as a handpiece with which the contact laser scalpel can be moved or used by hand.

7. The laser surgery apparatus according to claim 1, wherein said uncoated contact surface has a diameter of less than 100 μm.

8. The laser surgery apparatus according to claim 1, wherein the optical fiber tip has a blade shape of a mechanical scalpel.

9. The laser surgery apparatus according to claim 1, wherein the optical fiber tip has a shape selected from the group consisting of a wedge shape, a hook shape, a conical shape, a chisel shape, a shape of a side cutting blade and a needle shape.

10. The laser surgery apparatus according to claim 1, wherein said guiding surface is a coated surface that is reflective to laser radiation and provided such that laser radiation guided by said optical fiber to said optical fiber tip will be reflected by said coated surface and emitted through said uncoated contact surface.

11. The laser surgery apparatus according to claim 10, wherein the coated surface has a coating selected from the group consisting of a metallic coating, a stacked oxide coating, and a dielectric coating for the infrared region.

12. The laser surgery apparatus according to claim 10, wherein the optical fiber tip is wedge-shaped having a planar rectangular uncoated end surface at a distal end of the contact laser scalpel forming the uncoated contact surface and a coated slant surface formed at an angle with respect to the end surface and converging in a direction of the end surface.

13. The laser surgery apparatus according to claim 10, the contact laser scalpel further comprising a second optical fiber terminating at a second optical fiber tip, wherein
   a) the second optical fiber tip is arranged in parallel and adjacent to the optical fiber tip, and
   b) the two optical fiber tips are conical-shaped, the conical surface of each optical fiber tip being coated except for a line segment joining an apex to a perimeter of a large diameter end portion of the conical surface, and uncoated line segments of the two optical fiber tips are arranged facing each other and forming a V-shaped uncoated contact area.

14. The laser surgery apparatus according to claim 1, wherein said guiding surface is an uncoated surface having a tapering angle such that at least 30% of laser radiation guided by said optical fiber to said optical fiber tip will be reflected by said guiding surface and subsequently emitted through said uncoated contact surface.

15. The laser surgery apparatus according to claim 14, wherein said optical fiber is a sapphire ($Al_2O_3$) fiber and said tapering angle is lower than 15°.

16. The laser surgery apparatus according to claim 1, wherein the optical fiber tip is made of $Al_2O_3$, $Y_3Al_5O_{15}$, $GeO_2$, $TeO_2$, $ZrF_4$, $InF_3$, $AlF_3$, endcapped PCF or endcapped hollow core fibers, or other infrared waveguiding fibers.

17. The laser surgery apparatus according to claim 1, wherein a diameter of a guiding fiber core of the optical fiber is in the range of 4-1000 µm prior to any tapering or structuring of the fiber tip.

18. The laser surgery apparatus according to claim 1, wherein the optical fiber is a single mode fiber and a diameter of a fiber core is in a range of 1 to 100 µm.

19. The laser surgery apparatus according to claim 1, wherein said uncoated contact surface has a diameter of less than 10 µm.

20. A method for cutting a tissue comprising:
providing the laser surgery apparatus according to claim 1; and
contacting the tissue to be cut with the uncoated contact surface of the optical fiber tip of the contact laser scalpel and making an incision by heating the contacted tissue by pulsed IR laser radiation of the laser source emitted from the uncoated contact surface, wherein water in the contacted tissue is heated to at least one of a temperature in a range of 50° C. to <200° C. and a temperature below a vaporization or boiling point temperature of the contacted tissue in a range from 100 to 1500° C. for tissue varying from soft tissue to bony and calcified structures/teeth and thereby reducing a shear force needed for cutting the tissue.

21. The method according claim 20, further comprising:
cutting the heated tissue in a region below the uncoated contact surface of the optical fiber tip by locally exerting a mechanical shearing force with the optical fiber tip.

22. The laser surgery apparatus according to claim 1, further comprising:
d) an input terminal for selecting a type of tissue to be cut, and
e) a laser source control unit configured for controlling a wavelength, the pulse durations and/or a repetition rate of the generated laser radiation based on the selected type of tissue,
wherein the laser source control unit is configured to set the wavelength, the pulse durations and the repetition rate of the laser source such that when said uncoated contact surface of the optical fiber tip contacts a tissue to be cut a surgical incision can be made by providing local impulsive heating of water in the contacted tissue by pulsed IR laser radiation of the laser source and by simultaneously or subsequently applying a shear force using the uncoated contact surface of the optical fiber tip as a mechanical cutting edge to locally cut the heated tissue.

23. The laser surgery apparatus according to claim 22, wherein the laser source control unit is configured to set the wavelength, the pulse durations and the repetition rate of the laser source such that when said uncoated contact surface of the optical fiber tip contacts the tissue to be cut, a fluence of the pulsed laser radiation is under an ablation threshold of human tissue.

24. The laser surgery apparatus according to claim 22, wherein the laser source control unit is configured to set the wavelength, the pulse durations and the repetition rate of the laser source such that when said uncoated contact surface of the optical fiber tip contacts a tissue to be cut, pulsed IR laser radiation of the pulsed laser source emitted from the uncoated contact surface of the optical fiber tip heats water in the contacted tissue to a temperature in a range of 50° C. to <200° C. and/or heats biological tissue up to a temperature below a vaporization temperature of the biological tissue in a range from 100 to 1500° C. for tissue varying from soft tissue to bony and calcified structures/teeth and thereby reduces a shear force needed for cutting the tissue to be cut.

* * * * *